United States Patent [19]
Jiang et al.

[11] Patent Number: 5,807,983
[45] Date of Patent: Sep. 15, 1998

[54] GNRH ANTAGONIST BETIDES

[75] Inventors: Guangcheng Jiang; Jean E. F. Rivier, both of La Jolla, Calif.

[73] Assignee: The Salk Institute for Biological Studies, San Diego, Calif.

[21] Appl. No.: 598,424

[22] Filed: Feb. 8, 1996

Related U.S. Application Data

[63] Continuation-in-part of Ser. No. 579,216, Dec. 28, 1995.

[51] Int. Cl.$^6$ ..................................................... C07K 7/23
[52] U.S. Cl. ............................. 530/313; 530/328; 514/15
[58] Field of Search ................................. 530/313, 328; 514/15

[56] References Cited

U.S. PATENT DOCUMENTS

| | | | |
|---|---|---|---|
| 5,169,932 | 12/1992 | Hoeger et al. | 530/313 |
| 5,169,935 | 12/1992 | Hoeger et al. | 530/328 |
| 5,296,468 | 3/1994 | Hoeger et al. | 514/15 |
| 5,506,207 | 4/1996 | Rivier et al. | 514/15 |
| 5,681,928 | 10/1997 | Rivier et al. | 530/333 |

OTHER PUBLICATIONS

Abstract, Rivier et al., "Betidamino Acids: Versatile and Constrined Scaffolds for Drug Discovery", L020, 14th American Peptide Symposium, Columbus, Ohio (Jun. 18–23, 1995).

Bock et al., "Differentially Protected Alpha–Aminoglycine", J. Org. Chem. 1986, vol. 51, pp. 3718–3720.

Abstract, Koerber et al., "Solvation Energy Effects on the Conformation of Normal and Methylated Peptides and Betides", P505, *14th American Peptide Symposium*, Columbus, Ohio (Jun. 18–23, 1995).

Abstract, Rivier et al., "Betidamino Acids: Versatile and Constrained Scaffolds for Drug Discovery", L020, *14th American Peptide Symposium*, Columbus, Ohio (Jun. 18–23, 1995).

Abstract, Rivier et al., "Betidamino Acids: Versatile and Constrained Novel Scaffolds for Drug Discovery", Western Biotech Conference (Oct. 18–21, 1995).

*Primary Examiner*—Cecilia J. Tsang
*Assistant Examiner*—Anish Gupta
*Attorney, Agent, or Firm*—Fitch, Even, Tabin & Flannery

[57] ABSTRACT

Betides having at least one betidamino acid are provided which have GnRH antagonistic properties. These antagonists may be used to regulate fertility and to treat steroid-dependent tumors, such as prostatic and mammary tumors. One particularly effective betide, which is an analog of the decapeptide GnRH that is highly soluble in water at physiologic pH, has the formula: Ac-D-2Nal-D-4Cpa-D-3Pal-Ser-Aph(acetyl)-D-Aph(acetyl)-Leu-D/L-Agl(methyl, isopropyl β-alanyl)-Pro-D-Ala-NH$_2$, and another has the formula Ac-D-2Nal-D-Cpa-D-3Pal-D/L-Agl(For)-Aph(Ac)-D-Aph(Ac)-Leu-ILys-Pro-D-Ala-NH$_2$.

20 Claims, No Drawings

GNRH ANTAGONIST BETIDES

This application is a continuation-in-part of U.S. Ser. No. 08/579,216 filed Dec. 28, 1995.

This invention was made with Government support under grant number HD-13527 and DK-26741 and contracts NO1-HD-3-3171 and NO1-HD-0-2906 awarded by the National Institutes of Health. The Government has certain rights in this invention.

This invention relates generally to peptide-like compounds which are antagonists of human gonadotropin releasing hormone (GnRH). More particularly, it relates to GnRH antagonist peptides that include at least one betidamino acid (as defined hereinafter); these compounds are referred to as betides and have advantageous physical, chemical and biological properties. In a more particular aspect, the present invention relates to decabetides which inhibit the gonadal function and the release of the steroidal hormones progesterone and testosterone, and to methods of administering such decabetides for such purpose and particularly to manage conditions resulting from the hypersecretion of gonadal steroids, as well as to prevent ovulation.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH was isolated and characterized as a decapeptide some 20 years ago, and it was found shortly thereafter that analogs of GnRH having a D-isomer instead of Gly in the 6-position, such as [D-Ala$^6$]-GnRH (U.S. Pat. No. 4,072,668) having the following formula:

pGlu-His-Trp-Ser-Tyr-D-Ala-Leu-Arg-Pro-Gly-NH$_2$, have greater binding affinity/strength to the receptor and greater biological potency than the native hormone.

Peptides are compounds which contain two or more amino acids in which the carboxyl group of one acid is linked to the amino group of the other acid. The formula for the GnRH analog represented above is in accordance with conventional representation of peptides where the amino terminus appears to the left and the carboxyl terminus to the right. The position of each amino acid residue is identified by numbering the amino acid residues from left to right. In the case of GnRH, the hydroxyl portion of the carboxyl group of glycine at the C-terminus has been replaced with an amino group (NH$_2$) i.e. the C-terminus is amidated. The abbreviations for the individual amino acid residues above are conventional and are based on the trivial name of the amino acid, e.g. pGlu is pyroglutamic acid, Glu is glutamic acid, His is histidine, Trp is tryptophan, Ser is serine, Tyr is tyrosine, Gly is glycine, Leu is leucine, Nle is norleucine, Orn is ornithine, Arg is arginine, Har is homoarginine, Pro is proline, Sar is sarcosine, Phe is phenylalanine, Ala is alanine, Val is valine, Nva is norvaline, Ile is isoleucine, Thr is threonine, Lys is lysine, Asp is aspartic acid, Asn is asparagine, Gln is glutamine, and Met is methionine. Except for glycine, amino acids of the peptides of the invention are of the L-configuration unless noted otherwise.

Betidamino acids are N'-mono-acylated (optionally, both N'-mono-acylated and either N-mono-alkylated or N,N'-dialkylated) derivatives of aminoglycine (Agl). Betidamino acid residues may be conveniently generated on solid supports in chain elongation peptide synthesis by the selective acylation of one of the two amino functions of orthogonally protected aminoglycine or N'-methyl-aminoglycine.

There are reasons for desiring to prevent secretion of gonadotropins in general in mammals and to prevent ovulation in female mammals, and the administration of GnRH analogs that are antagonistic to the normal function of GnRH have been used to suppress such secretion and to suppress or delay ovulation. For this reason, analogs of GnRH which are antagonistic to GnRH are being investigated for their potential use as suppressives, as contraceptives and for regulating conception periods. For example, GnRH antagonists may also be used for the treatment of precocious puberty and endometriosis and other such conditions which result from hypersecretion of gonadotropins. Such antagonists have also been found useful to regulate the secretion of gonadotropins in male mammals and can be employed to arrest spermatogenesis, e.g. as male contraceptives for treatment of male sex offenders, and for treatment of prostatic hypertrophy. More specifically, GnRH antagonists can be used to treat steroid-dependent tumors, such as prostatic and mammary tumors, and for the control of the timing of ovulation for in vitro fertilization. In the female, they can also be used to treat hirsutism.

There are a number of peptides that are known to cause histamine to be released from mast cells which cells are found in the skin, the gingiva and other locations throughout the body. As a result, inflammation is caused, often resulting in edema of the face and elsewhere on the skin. It was earlier found that certain GnRH antagonists that were effective in preventing ovulation had the undesirable adverse side effect of stimulating histamine release, generally rendering such GnRH analogs unacceptable for administration to humans. As a result, the design of GnRH analogs has generally been directed to providing peptides that retain the biological efficacy but do not exhibit such undesirable histamine release, see J. Rivier et al., *J. Med. Chem.*, 29, 1846–1851 (1986). In addition, it is sometimes felt to be important that a peptide analog should have long duration of action upon LH secretion, a property which is considered to be enhanced by resistance to proteolytic enzyme degradation in the body. However, in some other instances it may be important for an analog to exhibit high potency, for only a short duration of time, or at least for a period that can be fairly precisely determined.

In addition, to facilitate administration of these compounds to mammals, particularly humans, it is considered extremely advantageous for such GnRH antagonistic decapeptides to have high solubility in water at normal physiologic pH, i.e. about pH 5 to about pH 7.4. In International Application PCT/US95/02653 (WO 95/25741), the design and synthesis of GnRH antagonists having improved properties in various of these respects are described. Despite the attractive properties of these GnRH analogs, the search has continued for still further improved GnRH antagonists.

SUMMARY OF THE INVENTION

It has now been found that GnRH antagonist deca-betides having the following formula, and closely related analogs thereof, have improved pharmacological properties:

X-Xaa$_1$-D-Cpa-Xaa$_3$-Xaa$_4$-Xaa$_5$-Xaa$_6$-Xaa$_7$-Xaa$_8$-Pro-Xaa$_{10}$ wherein X is an acyl group of 7 carbon atoms or less; Xaa$_1$ is D-2Nal or a corresponding betidamino acid; Xaa$_3$ is D-3Pal or a corresponding betidamino acid; Xaa$_4$ is Ser or a corresponding betidamino acid; Xaa$_5$ is 4Aph(Q) or a corresponding betidamino acid; Xaa$_6$ is D-4Aph(Q) or a corresponding betidamino acid; Xaa$_7$ is Leu or a corresponding betidamino acid; Xaa$_8$ is ILys or a corresponding betidamino acid; Xaa$_{10}$ is D-Ala-NH$_2$ or a corresponding betidamino acid or equivalent; and Q is 3-amino 1,2,4 triazole(Atz) or acetyl (Ac); provided that at least one Xaa is betidamino acid. These antagonists are particularly useful to suppress the secretion of gonadotropins and as fertility regulators in humans. They have excellent solubility in aqueous buffers at physiologic pHs and acceptable side effects of stimulating histamine release, i.e. better than the GnRH superagonists which are now being clinically used. The presence of at least one betidamino acid is believed to be responsible for including high solubility and good biopotency. As a result, these betides find particular use in administration to mammals, especially humans, as fertility regulators and for the treatment of pathological conditions such as precocious puberty, hormone dependent neoplasia, dysmenorrhea, endometriosis and steroid-dependent tumors. Betides which exhibit good biopotency of only short and definite duration are useful for in vitro fertilization and similar regimens where it is advantageous for the suppression of LH and FSH to be effective for only a fairly precise period of time which can be easily determined.

These GnRH antagonists are readily soluble in the physiologic pH range of about 5 to about 7.4; therefore, they can be formulated and administered in concentrated form, particularly at a pH between about 5 and about 7. These GnRH antagonist betides exhibit effective suppression of LH, and certain betides having long duration of potency are considered to be particularly effective for the contraceptive treatment of male mammals and for the treatment of steroid-dependent tumors.

DETAILED DESCRIPTION OF THE PREFERRED EMBODIMENTS

U.S. Pat. No. 5,169,932, issued Dec. 8, 1992, discloses the design and synthesis of a number of GnRH antagonists wherein the side chains of selected residues are reacted to create cyanoguanidino moieties, some of which subsequently spontaneously convert to a desired heterocycle, e.g. a 3-amino, 1,2,4 triazole(Atz). The cyanoguanidino moieties are built upon the omega-amino group in an amino acid side chain such as lysine, ornithine or 4-amino phenylalanine (Aph) or an extended chain version thereof, such as 4-amino homophenylalanine (Ahp). GnRH antagonists having such significantly modified or unnatural amino acids in the 5- and 6-positions have good biological potency, and those built upon Aph, or upon its equivalent Ahp, are considered to be representative of these and are preferred. The aforementioned International application discloses biopotent GnRH antagonists wherein the amino-substituted phenylalanine side chain is acetylated. It has now been found that, by the substitution of at least one corresponding betidamino acid into such GnRH antagonists, particularly advantageous overall properties are obtained.

Over the last decade, the particular properties of each of the 10 residues in the sequence of GnRH, from the standpoint of creating an effective antagonist, have been studied in depth, and as a result of these studies, it has been discovered that there are various equivalent residues that can be chosen and that substitutions of one of these equivalents for another does not significantly detract from the biological potency of decapeptide GnRH antagonists. Such equivalent substitution may be made in the GnRH antagonist betides of the present invention.

For example, it has become generally accepted that the inclusion of a para-substituted D-Phe or a 2,4 chloro-disubstituted D-Phe or a pentamethyl(Me$_5$)D-Phe residue in the 2-position adds significantly to GnRH antagonist activity and that the specific identity of the ring substituent is of only relatively minor importance when selected from among the following: chloro, fluoro, bromo, nitro, methyl and alkoxy. Therefore, such residues in the 2-position are considered to be the equivalent of 4ClD-Phe(D-4Cpa) which is commonly used. The N-terminus should be N-acylated, preferably by acetyl, but alternatively other acyl groups having up to 7 carbon atoms, e.g. formyl, acrylyl and benzoyl, may be present. Other longer acyl groups are considered to be equivalents but are less preferred. The C-terminus is preferably D-Ala-NH$_2$ or the betide equivalent thereof; however, Gly-NH$_2$, NHCH$_2$CH$_3$, Agl-NH$_2$, N'CH$_3$Agl-NH$_2$ and AzaGly-NH$_2$ may instead be used as they are considered equivalents.

The present invention is considered to provide a preferred family of GnRH antagonist betides represented by the following formula: Ac-Xaa$_1$-D-Cpa-Xaa$_3$-Xaa$_4$-Xaa$_5$-Xaa$_6$-Xaa$_7$-Xaa$_8$-Pro-Xaa$_{10}$ wherein Xaa$_1$ is D-2Nal or a corresponding betidamino acid; Xaa$_3$ is D-3Pal or a corresponding betidamino acid; Xaa$_4$ is Ser or a corresponding betidamino acid; Xaa$_5$ is 4Aph(Q) or a corresponding betidamino acid; Xaa$_6$ is D-4Aph(Q) or a corresponding betidamino acid; Xaa$_7$ is Leu or a corresponding betidamino acid; Xaa$_8$ is ILys or a corresponding betidamino acid; Xaa$_{10}$ is D-Ala-NH$_2$ or a corresponding betidamino acid or equivalent; and Q is 3-amino 1,2,4 triazole(Atz) or acetyl (Ac); provided that at least one Xaa is betidamino acid.

By D-Nal is meant the D-isomer of alanine which is substituted by naphthyl on the β-carbon atom, i.e., also referred to as 3-D-Nal. Preferably D-2Nal is employed wherein the attachment to naphthalene is at the 2-position on the ring structure; however, D-1Nal may also be used. D-Cpa represents chloroD-Phe, and D-4Cpa, i.e. 4ClD-Phe is preferred. D-Pal represents the D-isomer of alanine which is substituted by pyridyl on the β-carbon atom; preferably, the linkage is to the 3-position on the pyridine ring, i.e. D-3Pal (nicotinoylAla), although D-2Pal(isonicotinoylAla) is considered equivalent. By Aph is meant 4NH$_2$Phe wherein the amino substituent on the phenyl ring is at the 4-position; 4NH$_2$-homophenylalanine is considered its equivalent. By ILys is meant isopropyl lysine whenever the ε-amino group of Lys is alkylated. Gly-NH$_2$, —NHCH$_2$CH$_3$, Agl-NH$_2$, N'CH$_3$Agl-NH$_2$ and AzaGly-NH$_2$ are considered to be equivalents to D-Ala-NH$_2$ at the C-terminus.

Generally the corresponding betidamino acid residues with respect to D-2Nal are identified by the formula:

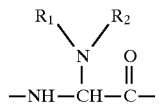

with R$_1$ being H or CH$_3$, and R$_2$ being naphthoyl.

Generally the corresponding betidamino acid residues with respect to D-3Pal are D- and D/L-Agl(nicotinoyl), Agl(isonicotinoyl), Agl(methyl,nicotinoyl) and Agl(methyl, isonicotinoyl).

Generally the corresponding betidamino acid residues with respect to Ser are identified by the formula:

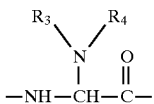

with $R_3$ being H or $CH_3$ and $R_4$ being formyl or hydroxyacetyl.

Generally the corresponding betidamino acid residues with respect to 4Aph(Q) are identified by the formula:

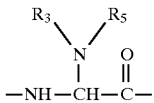

with $R_3$ being H or $CH_3$, $R_5$ being 4NH(Q)-benzoyl and Q being Atz or Ac or an equivalent thereof as hereinbefore mentioned.

Generally the corresponding betidamino acid residues with respect to Leu are L- or D/L-Agl($CH_3$,isobutyryl), L- or D/L-Agl(acetyl) and L- or D/L-Agl($CH_3$,acetyl).

Generally the corresponding betidamino acid residues with respect to ILys are identified by the formula:

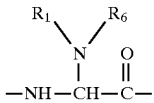

with $R_1$ being H or $CH_3$ and $R_6$ being (R)β-alanyl, (R)glycl or guanidinoacetyl, with R being H or isopropyl(Ipr), with Ipr being preferred.

Generally, $Xaa_{10}$ should be D-Ala-$NH_2$ or a residue having the formula:

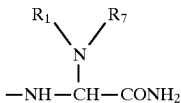

with $R_1$ being H or $CH_3$ and $R_7$ being H or formyl.

A preferred subgenus of GnRH antagonists has the formula:

Ac-$Xaa_1$-D-4Cpa-$Xaa_3$-Ser-4Aph(Q)-D-4Aph(Q)-Leu-ILys-Pro-$Xaa_{10}$ wherein:

$Xaa_1$ is (a)

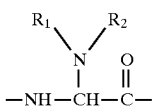

with $R_1$ being H or $CH_3$, and $R_2$ being naphthoyl; preferred are D- or D/L-Agl(2-naphthoyl) and Agl(methyl,2-napthoyl); or (b) D-2Nal;
wherein
$Xaa_3$ is (a) D- or D/L-Agl(nicotinoyl) or D- or D/L-Agl(isonicotinoyl), or (b) D-3Pal;
wherein Q is atz or Ac or an equivalent as mentioned; and wherein $Xaa_{10}$ is (a)

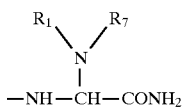

with $R_1$ being H or $CH_3$ and $R_7$ being H or formyl; provided however that at least one of $Xaa_1$, $Xaa_3$ and $Xaa_{10}$ is (a).

An additional preferred subgenus of GnRH antagonists has the formula:

Ac-D-2Nal-D-4Cpa-D-4Pal-$Xaa_4$-4Aph(Q)-D-4Aph(Q)-Leu-$Xaa_8$-Pro-$Xaa_{10}$ wherein:

$Xaa_4$ is (a)

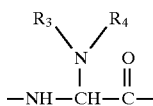

with $R_3$ being H or $CH_3$, and $R_4$ being formyl; provided however that at least one of $Xaa_1$, $Xaa_3$ and $Xaa_{10}$ is (a). or hydroxyacetyl; or (b) Ser;
wherein
$Xaa_8$ is (a)

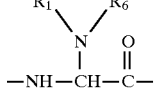

with $R_1$ being H or $CH_3$ and $R_6$ being (isopropyl)β-alanyl, (isopropyl)glycyl or guanidinoacetyl; or (b) Ilys; and
wherein
$Xaa_{10}$ is (a)

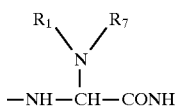

with $R_1$ being H or $CH_3$ and $R_7$ being H or formyl; provided however that at least one of $Xaa_4$, $Xaa_8$ and $Xaa_{10}$ is (a).

Another preferred subgenus of GnRH antagonists has the formula:

Ac-D-2Nal-D-4Cpa-$Xaa_3$-Ser-4Aph(Ac)-D-4Aph(Ac)-Leu-$Xaa_8$-Pro-$Xaa_{10}$ wherein $Xaa_3$ is (a) D- or D/L-Agl(nicotinoyl) or D- or D/L-Agl(isonicotinoyl), or (b) D-3Pal;

wherein $Xaa_8$ is (a)

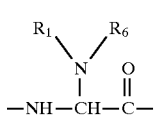

with $R_1$ being H or $CH_3$, and $R_6$ being (isopropyl)β-alanyl, isopropyl glycyl or guanidinoacetyl; or (b) ILys; and
wherein Xaa$_{10}$ is (a)

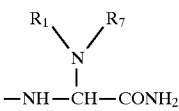

with R$_1$ being H or CH$_3$ and R$_7$ being formyl; provided however that at least one of Xaa$_8$ and Xaa$_{10}$ is (a).

The compounds of the present invention can be synthesized by classical peptide solution synthesis, but are preferably synthesized by a solid phase technique. A chloromethylated resin or a hydroxymethylated resin may be used; however, a methylbenzhydrylamine(MBHA) resin, a benzhydrylamine (BHA) resin or some other suitable resin known in the art which directly provides a C-terminal amide upon cleavage is preferably employed. Should equivalent peptides having a substituted amide at the C-terminus be desired, they are preferably synthesized using an N-alkylamino methyl resin as taught in U.S. Pat. No. 4,569, 967, issued Feb. 11, 1986. Solid phase synthesis is conducted in a manner to stepwise add amino acids to the chain in the manner set forth in detail in the U.S. Pat. No. 4,211,693. Side-chain protecting groups, as are well known in the art, are preferably included as a part of any amino acid which has a particularly reactive side chain, which amino acids are to be coupled into the chain being built upon the resin. Such synthesis provides the fully protected intermediate peptidoresin.

One example of a chemical intermediate for synthesizing a betide analog of GnRH having a betide residue in the 3-position is represented by the formula: $X^1$-D-2Nal-4ClD-Phe-D/L-Agl($X^3$)-Ser($X^2$)-Aph($X^3$)-D-Aph($X^3$)-Leu-ILys($X^4$)-Pro-$X^5$ wherein $X^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by $X^1$ are (1)acyl-type protecting groups, such as formyl(For), trifluoroacetyl, phthalyl, p-toluenesulfonyl(Tos), benzoyl(Bz), benzenesulfonyl, dithiasuccinoyl(Dts) o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxy-carbonyl (ClZ), p-nitrobenzyloxycarbonyl, p-bromobenzyloxycarbonyl and p-methoxybenzyloxycarbonyl; (3)aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7)trialkylsilane groups, such as trimethylsilane. The preferred α-amino protecting group is Boc.

$X^2$ is a protecting group for the hydroxyl side chain of Ser, e.g. Ac, Bz, trityl, DCB or benzyl ether(Bzl) and is preferably Bzl.

$X^3$ is a protecting group for the side chain amino group of Agl or Aal or the like which is not removed when the α-amino protecting group is removed. Illustrative examples include (1) base-labile groups, such as Fmoc, or some other weak-acid stable, aromatic urethane-type protecting group; (2) thiol-labile groups, such as dithiasuccinoyl(Dts) which may be removed or cleaved by thiolysis; (3) hydrazine-labile groups, such as phthaloyl(Pht) which is cleaved by hydrazinolysis; (4) nucleophile-labile groups, such as o-nitrophenyl-sulfenyl(Nps) and the like which are cleaved by thioacetamide or by weak acids or their salts; (5) photolabile groups which are cleaved by photolysis; and (6) groups selectively removable by reduction, such as Dts. Fmoc is preferred for a Boc SPPS strategy. $X^3$ can also be an acyl group that constitutes the ultimate side chain of the desired betidamino acid. Depending on the nature of the acyl group, additional protection may be required for this group.

$X^4$ is an acid-labile protecting group for a primary or secondary amino side chain group, such as Z or 2C1Z.

$X^5$ may be Gly-NH-[resin support], D-Ala-NH-[resin support], Agl($X^3$)-NH-[resin support] or N(A)-[resin support]; $X^5$ may also be an amide either of Gly or of D-Ala or a substituted amide attached directly to Pro.

The criterion for selecting side chain protecting groups $X^2$ and $X^4$ is that the protecting group should generally be stable to the reagent under the reaction conditions selected for removing the α-amino protecting group (preferably Boc) at each step of the synthesis. These protecting groups generally should not be split off under coupling conditions but should be removable upon completion of the synthesis of the desired amino acid sequence under reaction conditions that will not alter the peptide chain. The protecting groups initially employed for betidamino acids and for the 5- and 6-position residues are preferably removed prior to cleavage from the resin, as explained hereinafter.

When the $X^5$ group is D-Ala-NH-[resin support], an amide bond connects D-Ala to a BHA resin or to a MBHA resin.

When the N-terminus is to be acetylated, for example, it is possible to employ acetyl as the $X^1$ protecting group for the a-amino group of β-D-Nal in the 1-position by adding it to the amino acid before it is coupled to the peptide chain; however, a reaction is preferably carried out with the betide on the resin. After deblocking the α-amino group and while desired side chain groups remain protected, acetylation is preferably carried out by reacting with acetic anhydride, alternatively reaction can be carried out with acetic acid, in the presence of diisopropyl or dicyclohexyl carbodiimide (DIC or DCC), or by some other suitable acylation reaction as known in the art.

Thus, the invention also provides a preferred method for making a GnRH antagonist betide having the formula: $X^1$-D-2Nal-D-Cpa-D-3Pal-Ser($X^2$)-Aph($X^3$)-D-Aph($X^3$)-Leu-ILys($X_4$)-Pro-$X^5$ wherein at least one of the residues in positions 1, 3–8 or 10 is substituted by a corresponding betidamino acid, which method comprises (a) forming an intermediate peptide having the formula: $X^1$ -D-2Nal-D-Cpa-D-3Pal-Ser($X^2$)-Aph($X^3$)-D-Aph($X^3$)-Leu-Lys($X^4$)-Pro-$X^5$ wherein at least one of the residues is substituted by a betidamino acid that is created by originally coupling a differentially protected aminoglycine into the chain and then deprotecting and acylating the side chain amino group; $X^1$ is hydrogen or an α-amino protecting group; $X^2$ is hydrogen or a protecting group for a hydroxyl group of Ser; $X^3$ is hydrogen or a base-labile, hydrazine-labile or other appropriately labile protecting group for an amino group; $X^4$ is an acid-labile protecting group for an amino side chain; $X^5$ is D-Ala-NH-[resin support] or N(A)-[resin support]; (b) removing $X^3$ from Aph and D-Aph to deprotect a side chain primary amino group of these amino acid residues of said intermediate peptide; (c) reacting said deprotected side chain primary amino groups to either acetylate said residue or to build said residue into one having an amino-triazole moiety; (d) either separately or simultaneously removing $X^3$ from the Agl residue and appropriately acylating the side chain amino group; and (e) splitting off any remaining protecting groups and/or cleaving from resin support included in $X^5$.

As previously indicated, betidamino acids are monoacylated aminoglycine derivatives, wherein the side chain can closely resemble a natural amino acid side chain (so as to generally mimic that α-amino acid) with or without a lower alkyl (e.g. methyl) substitution on the β-carbon atom. The GnRH antagonist betides of the present invention are preferably synthesized by utilizing a building block in the form of a bis-protected α-amino-glycine in a conventional chain elongation process. The amino function that is not part of the backbone is referred to as the beta-site amino group, and it is acylated after being selectively deprotected. Acylation is accomplished by reaction with carboxylic acids (with a coupling agent), active esters or anhydrides, mixed or symmetric, or with an acyl chloride. Equivalent reactions can alternatively be carried out with isocyanates, isothiocyanates or sulfonyl chlorides to create equivalent betidamino acids.

Purification of the final betide is effected by ion exchange chromatography on a CMC column, followed by partition chromatography using the elution system: n-butanol; 0.1N acetic acid (1:1 volume ratio) on a column packed with Sephadex G-25, or by using HPLC, as known in the art and specifically set forth in J. Rivier, et al. *J. Chromatography*, 288 (1984) 303–328.

The GnRH antagonists of the invention are effective at levels of less than 100 micrograms per kilogram of body weight, when administered subcutaneously at about noon on the day of proestrus, to prevent ovulation in female rats. For prolonged suppression of ovulation, it may be necessary to use dosage levels in the range of from about 0.1 to about 2.5 milligrams per kilogram of body weight. These analogs are particularly soluble at physiological pHs and thus can be prepared as relatively concentrated solutions for administration. The antagonists are also effective to arrest spermatogenesis when administered to male mammals on a regular basis and can thus be used as contraceptives. Since these compounds will reduce testosterone levels (an undesired consequence in the normal, sexually active male), it may be desirable to administer replacement dosages of testosterone along with the GnRH antagonist. These antagonists can also be used to regulate the production of gonadotropins and sex steroids for other purposes as indicated hereinbefore.

Betides provided by the invention, relative to the corresponding non-betide peptides, are particularly soluble at physiological pHs. Thus, the betides of the invention can be prepared as relatively concentrated solutions for administration, particularly for subcutaneous injection. These betides are well-tolerated in the body and exhibit a lesser tendency to gel and remain at the point of injection than the counterpart non-betide peptides when administered subcutaneously. Generally pharmaceutical compositions including such betides and a suitable pharmaceutically acceptable excipient can be administered iv, ip, subcutaneously or the like at levels of between about 0.001 mg to about 2.5 mgs per Kg of body weight per day.

Although the appropriately protected betidamino acid can be synthesized and then employed in a chain elongation peptide synthesis, synthesis is preferably effected by incorporating an appropriately protected α-aminoglycine or N'-methylaminoglycine, i.e. Agl(Me) at a particular location of interest. This strategy is accomplished by reacting the deprotected side chain amino group with the desired acylating agent. When α-aminoglycine is employed, it may be optionally alkylated prior to the acylation reaction.

In many of the following formulas for GnRH antagonists, the residues which appear in positions 5 and 6 and/or the betidamino acid residues are sometimes defined in terms of the original amino acid residue having a side chain amino group, e.g. p-aminophenyl-alanine (Aph) or Agl, plus the modification to the amino group which is set forth in the accompanying parentheses. Preferably, the suitably protected Agl or Agl(Me) building block, and the Aph building blocks when the betidamino acids are located in other than the 5- and 6-positions, are originally incorporated in the main peptide chain, for example the respective L- or D-isomer of Aph or D/L Agl, and the side chain is then modified to form the desired residue while a part of the peptide chain that is still attached to the resin. Any such modification of Aph or the like is appropriately coordinated with the modification of Agl. Such may take place separately, either before or after the modification to create the betide, or simultaneously therewith if the same modification, e.g. acylation, is being made to several residues. However, a suitably protected betidamino acid can alternatively be added to the growing peptide chain as a part of the usual chain elongation process, if desired.

The present invention is further described by the examples which follow. Such examples, however, are not to be construed as limiting in any way either the spirit or the scope of the present invention. The following examples illustrate GnRH antagonist compounds embodying various features of the invention, and all of these compounds include at least one D-isomer amino acid residue.

EXAMPLE 1

The peptide having the formula: Ac-D-2Nal-D-4Cpa-D-3Pal-Ser-Aph(Ac)-D-Aph(Ac)-Leu-ILys-Pro-D-Ala-NH$_2$ has been found to exhibit very good biological properties as a GnRH antagonist, and it is now referred to as Acyline. It has now been found that certain betides patterned after this decapeptide having one or more corresponding betidamino acids in the sequence have improved properties.

The following decabetide [Ac-D-2Nal$^1$, D-4Cpa$^2$, D/L-Agl(nicotinoyl)$^3$, Aph(Ac)$^5$, D-Aph(Ac)$^6$, ILys$^8$, D-Ala$^{10}$]-GnRH (Betide No. 1) is synthesized by solid-phase synthesis. This betide has the following formula: Ac-D-2Nal-(4Cl) D-Phe-γ-(3-pyridyl)amidoGly-Ser-Aph(acetyl)-D-Aph(acetyl)-Leu-Lys(isopropyl)-Pro-D-Ala-NH$_2$.

About 3 grams (0.76 mM/g) of MBHA resin are initially used, and Boc-protected D-Ala is coupled to the resin over about a 100 minute period in N-methylpyrrolidone(NMP)/CH$_2$Cl$_2$ using about 5 millimoles of Boc derivative and diisopropylcarbodiimide (DIC) as an activating or coupling reagent. The D-Ala residue attaches to the MBHA residue by an amide bond.

Following the coupling of each amino acid residue, washing, deblocking and coupling of the next amino acid residue is carried out in accordance with the following schedule using an automated machine, which schedule may be used for a synthesis being carried out upon about 3 grams of resin:

| STEP | REAGENTS AND OPERATIONS | MIX TIMES MIN. |
|---|---|---|
| 1 | CH$_2$Cl$_2$ wash-80 ml. (2 times) | 1 |
| 2 | Methanol (MeOH) wash-30 ml. (2 times) | 1 |
| 3 | CH$_2$Cl$_2$ wash-80 ml. (3 times) | 1 |
| 4 | 50% TFA plus 5% 1,2 ethanedithiol in CH$_2$Cl$_2$-70 ml. (2 times) | 15 |
| 5 | Isopropyl alcohol + 1% ethanedithiol wash-80 ml. (2 times) | 1 |
| 6 | TEA 12.5% in CH$_2$Cl$_2$-70 ml. | 1 |
| 7 | MeOH wash-40 ml. (2 times) | 1 |
| 8 | TEA 12.5% in CH$_2$Cl$_2$-70 ml. (2 times) | 1 |
| 9 | CH$_2$Cl$_2$ wash-80 ml. (3 times) | 1 |
| 10 | Boc-amino acid (5 mmoles) in 30 ml. of CH$_2$Cl$_2$ (DCM) or dimethylformamide (DMF): DCM or NMP:DCM, depending upon the solubility of the particular protected amino acid, plus DIC or DCC (5 mmoles) in CH$_2$Cl$_2$ | 90–120 |
| 11 | MeOH wash-40 ml. (2 times) | 1 |
| 12 | Triethylamine (TEA) 12.5% in CH$_2$Cl$_2$-70 ml. | 1 |
| 13 | MeOH wash-30 ml. (2 times) | 1 |
| 14 | DCM wash-80 ml. (2 times) | 1 |

The above schedule is used for coupling of each of the amino acids of the peptide of the invention after the first amino acid has been attached. N$^\alpha$Boc protection is used for each of the amino acids coupled throughout the synthesis. N$^\alpha$Boc-β-D-2Nal is prepared by a method known in the art, e.g. as described in detail in U.S. Pat. No. 4,234,571, issued Nov. 18, 1980; it is also commercially available from SyntheTech, Or, U.S.A. The side chain primary amino groups of Aph in the 5-position and of D-Aph in the 6-position are protected by Fmoc. Benzyl ether (Bzl) is preferably used as a side chain protecting group for the hydroxyl group of Ser; however, Ser may be coupled without side chain protection. Boc-Lys(Ipr,Z) is used for the 8-position residue.

After adding Ser for the 4-position residue as N$^\alpha$Boc-Ser (Bzl), the following intermediate is present: Boc-Ser(Bzl)-Aph(Fmoc)-D-Aph(Fmoc)-Leu-Lys(Ipr,Z)-Pro-D-Ala-NH-[MBHA resin support]. The side chains on the amino acid residues in the 5- and 6-positions are then modified by simultaneously acetylating them after first removing the side-chain protection. The Fmoc protecting group is removed from both residues by treatment with 20 percent piperidine in DMF(10 ml) for about 30 minutes; the intermediate is preferably washed with DMF and then treated with more piperidine/DMF for another 30 minutes. After preferably washing the peptidoresin with DMF, the newly freed amino groups are treated with a large excess of acetic anhydride in DCM for 15 minutes or until complete as checked using a ninhydrin test, at room temperature to acetylate both side chains. The peptide resin is then subjected to the standard wash.

Following completion of the acetylation of the Aph residues, Boc and Fmoc-protected D/L-aminoglycine is coupled to the chain for the residue in the 3-position. Once added, the Boc protection is removed, the final two residues are subsequently added to complete the chain. After deblocking the α-amino group at the N-terminus using trifluoroacetic acid (TFA), acetylation is achieved using a large excess of acetic anhydride in dichloromethane.

Following acetylation of the N-terminus, the Agl side chain is selectively deprotected and acylated with nicotinic acid in DCM for 4 hours to form the γ-3-pyridylamidoglycine residue using an appropriate coupling agent such as DCC.

The betidoresin is dried, and then cleavage of the betide from the resin and deprotection of the Ser and the Lys side chains is carried out at 0° C. with HF for about 40 min. Anisole is added as a scavenger prior to HF treatment. After the removal of HF under vacuum, the resin is washed twice with 100 ml. of ethyl ether. The cleaved betide is extracted from the resin with equal parts of CH$_3$CN and H$_2$O, repeating the process and using 100 ml. each time. The extracts are pooled and lyophilized, and they provide a crude betide powder.

Purification of the betide is then effected by preparative high performance liquid chromatography (HPLC), as known in the art and specifically set forth in J. Rivier, et al. *J. Chromatoaraphy*, 288, 303–328 (1984). The first preparative RP-HPLC separation uses a TEAP (triethylammonium phosphate) buffer system. This separation is repeated using the same buffer system with a slightly different gradient, and a final separation is carried out using a 0.1% TFA (trifluoroacetic acid) gradient, all as described in detail in the *J. Chromatography* article. Two betides respectively having the L- and D-isomers of Agl at position 3 are separated and desalted using this procedure.

The two betide fractions are judged to be homogeneous using capillary zone electrophoresis (CZE), as well as by using reversed-phase high performance liquid chromatography (RP-HPLC) and an aqueous triethylammonium phosphate buffer plus acetonitrile. The purity is estimated to be about 97%–98% . Amino acid analysis of each resultant, purified betide is consistent with the formula for the prepared structure, showing substantially integer-values for each amino acid in the chain; liquid secondary ion mass spectrometry (LSIMS) is also consistent. The optical rotation is measured on a photoelectric polarimeter as $[\alpha]_D^{20}$= −34.0° and −24.4°±1.0 (c=1, 50% acetic acid) for the two stereoisomers, isomers (1) and (2). LSIMS analysis showed the expected mass of 1561.8 Da for each isomer.

The betide is assayed in vivo to determine its effectiveness to prevent ovulation in female rats. In this test, a specified number of mature female Sprague-Dawley rats, e.g. five to ten, each having a body weight from 225 to 250 grams, are injected with a specified microgram dosage of the betide in bacteriostatic water at about noon on the day of proestrus. Proestrus is the afternoon of ovulation. A separate female rat group is used as a control to which the peptide is not administered. Each of the control female rats ovulates on the evening of proestrus; the number of the rats treated which ovulate is recorded. In vivo testing of the two isomeric betides shows that, at a dosage of 2.5 microgram, 0 out of 7 and 0 out of 5 rats treated ovulate with respect to isomers (1) and (2), respectively. At a dosage of 1.0 microgram for isomer (1), all 3 rats ovulate, while at a dosage of 1 μg of isomer (2), only 6 out of 14 rats ovulate and at 0.5 μg, 3 out of 4 rats ovulate. Examination of the rats shows that the betide was very well tolerated, with no significant gelling at the point of injection being detectable.

Hydrophilicity is tested by measuring retention using RP-HPLC with a gradient of 40% Buffer B to 75% Buffer B over 30 minutes, with Buffer A being TEAP pH 7.3 and Buffer B being 60% CH$_3$CN and 40% Buffer A. Betide No. 1 is more hydrophilic, eluting at 23.5 minutes compared to 24.1 minutes for Acyline. The betide is considered to be particularly useful because of its solubility in aqueous buffers at a pH of from about 5 to about 7 and its resistance to in vivo gelling, which renders it particularly suitable for administration by subcutaneous injection compared to other compounds of generally comparable biological efficacy. Moreover, Betide No. 1 exhibits fairly long-acting biopotency, suppressing circulating LH concentrations to levels that are less than 25% of control levels for 48 hours or more at a dose of 50 micrograms per rat.

EXAMPLE 1A

The synthesis set forth in Example 1 is repeated, substituting isonicotinoyl chloride in DCM for nicotinic acid and reacting for 4 hours to form the γ-4-pyridylamidoglycine residue. Cleavage from the resin and deprotection, followed by purification, are carried out as described in Example 1. The two distereomers of the betide Ac-β-D-2Nal-D-4Cpa-γ-(4-pyridyl)D/L-amidoGly-Ser-Aph(acetyl)-D-Aph (acetyl)-Leu-Lys(isopropyl)-Pro-D-Ala-NH$_2$ (Betide No. 1A) are separated in the RP-HPLC purification. Each is judged to be homogenous, and the purity of each is estimated to be greater than 80 percent. The optical rotations are measured on a photoelectric polarimeter as $[\alpha]_D^{20}$=−31.5° and 25.4°±1.0 (c=1, 50% acetic acid) respectively, for the two isomers. MS analysis showed the expected mass of 1561.8 Da for both isomers. Both of these betides are more hydrophilic than Acyline.

Assaying these two betides in the standard in vivo rat anti-ovulation test shows that, at dosages of 10 micrograms, 3 out of 7 and 0 out of 8 rats, respectively, ovulate; however, at a dosage of 2.5 micrograms, only the second isomer was bioactive, with only 2 out of 8 rats ovulating.

EXAMPLE 1B

The synthesis set forth in Example 1 is again repeated, but Fmoc(Me)-D/L-Agl(Boc) is coupled in the 3-position. After removal of the Fmoc protecting group as in Example 1, the intermediate is treated with nicotinic acid in DCM in the presence of HBTU or DCC for about 30 to 60 minutes at room temperature to acylate the methylamino side chain of the Agl residue. Cleavage from the resin and deprotection, followed by purification, are carried out as described in Example 1. The two distereomers of the betide Ac-β-D-2Nal-D-Cpa-γ-(3-pyridyl)methylD/L-amidoGly-Ser-Aph(acetyl)-D-Aph(acetyl)-Leu-Lys(isopropyl)-Pro-D-Ala-NH$_2$ (Betide No. 1B) are separated in the RP-HPLC purification. Each is judged to be homogenous, and the purity of each is estimated to be greater than 80 percent. MS analysis showed masses of 1575.80 Da and 1575.78 Da, which are in agreement with the calculated mass of 1575.76 Da. Both of these betides are more hydrophilic than Acyline.

Assaying these two betides in the standard in vivo rat anti-ovulation test shows that, at a dosage of 2.5 micrograms, only the second isomer was bioactive, with only 3 out of 8 rats ovulating. EXAMPLE 2

The betide having the formula Ac-D-2Nal-D-4Cpa-D-3Pal-D/L-Agl(methyl,formyl)-Aph(Ac)-D-Aph(Ac)-Leu-Lys(isopropyl)-Pro-D-Ala-NH$_2$ is synthesized using the synthesis as generally set forth in Example 1. Instead of coupling NαBoc-D/L-Agl(Fmoc) in the 3-position, Fmoc (Me)-D/L-Agl(Boc) is coupled in the 4-position. D-3Pal is coupled in the 3-position. In this synthesis, following the completion of the decapeptide and the acetylation of the N-terminus, the following peptide intermediate is obtained: Ac-D-2Nal-D-Cpa-D-3Pal-D/L-Agl(methyl,Fmoc)-Aph (Ac)-D-Aph(Ac)-Leu-Lys(Ipr,Z)-Pro-D-Ala-NH-[MBHA resin support]. The side chain on the Agl residue is then deprotected by removal of the Fmoc protection as in Example 1, and the intermediate is treated with excess formic acid and acetic anhydride for about 30–60 minutes at room temperature to acylate the side chain of the methylated Agl residue.

The betidoresin is then subjected to the standard wash, and cleavage from the resin and deprotection, followed by purification, are carried out as described in Example 1. The two distereomers of the betide Ac-D-2Nal-D-4Cpa-D-3Pal-D/L-(methyl,formyl)aminoGly-Aph(Ac)-D-Aph(Ac)-Leu-Lys(isopropyl)-Pro-D-Ala-NH$_2$ (Betide No. 2) are separated in the RP-HPLC purification. Each is judged to be homogeneous, and the purity of each is estimated to be greater than 90 percent. LSIMS analysis shows measured masses of 1559.82 Da and 1559.80 Da which are in agreement with the calculated mass of 1559.76 Da for this betide.

Assaying the betide isomers using the standard in vivo rat ovulation test shows that, at a dosage of 2.5 micrograms, 5 out of 8 rats ovulate with one isomer. The other distereomer is inactive at 2.5 micrograms, with 8 out of 8 rats ovulating.

EXAMPLE 2A

The synthesis as set forth in Example 2 is repeated to provide the betide Ac-D-2Nal-D-4Cpa-D-3Pal-D/L-Agl (HO-Ac)Aph(Ac)-D-Aph(Ac)-Leu-Lys(isopropyl)-Pro-D-Ala-NH$_2$. Upon deprotection of the Agl residue by removal of the Fmoc protection, a reaction is carried out using 2-hydroxy acetic acid in DMF/DCM for about 7 hours in the presence of DIC and 1-hyroxybenzotriazole to form the (2-hydroxyacetyl)amidoglycine residue in the 2-position of the betide. Cleavage from the resin and deprotection followed by purification are carried out as described in Example 1. The two distereomers of the betide (Betide No. 2A) are separated in the RP-HPLC purification. Each is judged to be homogenous, and the purity of each is estimated to be greater than 90%. MS analysis shows masses of 1575.84 Da and 1575.82 Da, respectively, which agree with the calculated mass of 1575.76 Da. The optical rotations of each are measured on a photoelectric polarimeter as $[\alpha]_D^{22}$= −34.0° and −30.0°±1.0(c=1, 50% acetic acid).

Assaying the isomers using the standard in vivo rat ovulation test shows that, at a dosage of 5 micrograms, 2 out of 8 rats ovulate for one of the isomers and 4 out of 8 rats ovulate for the other isomer.

EXAMPLE 2B

The synthesis as set forth in Example 2 is again repeated, to provide the betide Ac-D-2Nal-D-4Cpa-D-3Pal-D/L-Agl (formyl)-Aph(Ac)-D-Aph(Ac)-Leu-Lys(isopropyl)-Pro-D-Ala-NH$_2$. Cleavage from the resin and deprotection followed by purification are carried out as described in Example 1. The two distereomers of the betide (Betide No. 2B) are separated in the RP-HPLC purification. Each is judged to be homogenous, and the purity of each is estimated to be greater than 90%. The two stereoisomers are separated via RP-HPLC. MS analysis shows masses of 1545.81 Da and 1545.80 Da, respectively, which agree with the calculated mass of 1545.74 Da.

Assaying the isomers using the standard in vivo rat ovulation test shows that the first isomer is fully active (0/8) at a dosage of 5 micrograms, at a dosage of 1 μg, 2 out of 8 rats ovulate, and at 0.5 μg, 4 out of 5 rats ovulate. The other isomer is also fully active (0/8) at 5 μg, and at 1 μg, 6 out of 8 rats ovulate.

EXAMPLE 3

The betide having the formula Ac-D/L-Agl(2-naphthoyl)-D-4Cpa-D-3Pal-Ser-Aph(acetyl)-D-Aph(acetyl)-Leu-Lys (isopropyl)-Pro-D-Ala-NH$_2$ is synthesized using the synthesis as set forth in Example 1. Instead of coupling NαBoc- D/L-Agl(Fmoc) in the 3-position, it is coupled in the 1-position following acetylation of the Aph and D-Aph side chains. D-3Pal is coupled in the 3-position. In this synthesis, following the completion of the decapeptide and the acetylation of the N-terminus, the following peptide intermediate is obtained: Ac-D/L-Agl (Fmoc)-4Cl-D-Phe-D-3Pal-Ser (Bzl)-Aph (Ac)-D-Aph(Ac)-Leu-Lys(Ipr,Z)-Pro-D-Ala-NH-[MBHA resin support]. The side chain on the Agl residue is then deprotected as in Example 1, and the intermediate is treated with 10 millimoles of 2-naphthoyl chloride in a mixture of equal parts of DMF and DCM in the presence of a tertiary amine, i.e. diisopropylethylamine (DIPEA), for about 20 minutes at room temperature to acylate the side chain of the Agl residue.

The betidoresin is then subjected to the standard wash, and cleavage from the resin and deprotection, followed by purification using two different buffer systems, are carried out as described in Example 1. The two distereomers of the betide Ac-γ-(2-naphthoyl)amidoGly-4Cl-D-Phe-D-3Pal-Ser-Aph(acetyl)-D-Aph(acetyl)-Leu-Lys(isopropyl)-Pro-D-Ala-NH$_2$ are separated in the RP-HPLC purification. Each is judged to be homogeneous, and the purity of each is estimated to be greater than 90 percent. The optical rotations are measured on a photoelectric polarimeter as $[\alpha]_D^{20}$=--31.0° and -1.2°±1.0(c=1, 50% acetic acid) respectively, for the two isomers. MS analysis shows a mass for both isomers which agrees with the expected mass of 1561.8 Da.

Assaying the betides using the standard in vivo rat ovulation test shows that the first isomer (Betide No. 3) is fully active (0/8) at 2.5 μ, and at a dosage of 1 μg for the first isomer, 2 out of 7 rats ovulate. The second isomer is fully active (0/8) at 5 μg, but it is inactive (5/5) at 2.5 μg. Betide No. 3 exhibits fairly long-acting biopotency, showing effectiveness for 48 hours or more, similar to Betide No. 1.

EXAMPLE 3A

A betide similar to that synthesized in Example 3 is made, which has the formula Ac-D/L-Agl(2-naphthoyl)-D-4Cpa-D-3Pal-Ser-Aph(atz)-D-Aph(atz)-Leu-Lys(isopropyl)-Pro-D-Ala-NhD-Ala-NH$_2$. The synthesis set forth in Example 3 is used, but the Aph and D-Aph side chains, instead of being acetylated, are reacted to form the 3-amino 1,2,4 triazole moieties as described in U.S. Pat. No. 5,296,468. In this synthesis, following the completion of the decabetide and the acetylation of the N-terminus, the following betide intermediate is obtained: Ac-D/L-Agl(Fmoc)-4Cl-D-Phe-D-3Pal-Ser(Bzl)-Aph(atz)-D-Aph(atz)-Leu-Lys(Ipr,Z)-Pro-D-Ala-NH-[MBHA resin support]. The side chain on the Agl residue in the 1-position is then deprotected by removal of the Fmoc protection as in Example 1, and the intermediate is treated with 10 millimoles of 2-naphthoyl chloride as in Example 3 to acylate the side chain of the Agl residue.

The betidoresin is then subjected to the standard wash, and cleavage from the resin and deprotection, followed by purification using two different buffer systems, are carried out as described in Example 1. The two distereomers of the betide Ac-γ-(2-naphthoyl)amidoGly-4Cl-D-Phe-D-3Pal-Ser-Aph(atz)-D-Aph(atz)-Leu-Lys(isopropyl)-Pro-D-Ala-NH$_2$ (Betide No. 3A) are separated in the RP-HPLC purification. Each is judged to be homogeneous, and the purity of each is estimated to be greater than 90 percent. The optical rotations are measured on a photoelectric polarimeter as $[\alpha]_D^{20}$=-23.0° and +2.0°±1.0(c=1, 50% acetic acid) respectively, for the two isomers. MS analysis shows the expected mass of about 1642.01 Da for both isomers.

Assaying the betides using the standard in vivo rat ovulation test shows that the first isomer is fully active (0/8) at 2.5 μg and at a dosage of 1 μg, 5 out of 8 rats ovulate. The second isomer is fully active (0/3) at 2.5 μg, and at a dosage of 1 μg, 4 out of 8 rats ovulate.

EXAMPLE 3B

The synthesis set forth in Example 3A is generally repeated with one change to produce the betide Ac-D/L-Agl (methyl,2-naphthoyl)-D-4Cpa-D-3Pal-Ser-Aph(atz)-D-Aph (atz)-Leu-Lys(isopropyl)-Pro-D-Ala-NH$_2$. After the N-terminus is acetylated and the Fmoc protection is removed from the Agl residue, it is washed with NMP and the amino side chain is methylated. The newly freed aminomethyl groups are treated with (MeO-phenyl)$_2$-CHCl, which is referred to as Dod-Cl, in NMP plus diisopropyl ethylamine (DIEA) for 1–2 hours. After washing, the peptidoresin (about 1–2 g) is treated for 20 minutes with 6 mls of 36% formaldehyde and 10 mls of 1% acetic acid in NMP, adding 0.35 gram of cyanoborohydride (NaBH$_3$CN); at the end of 20 minutes, this treatment is repeated one more time. This reaction adds a single methyl group to the amino side chain. Details of the reaction are found in Kaljuste and Unden, *Int. J. Peptide Protein Res.*, 42, 118–124 (1993). Subsequent to such methylation, the Dod-Cl protecting group is removed, and the reaction with 2-naphthoyl chloride is carried out. Cleavage from the resin and deprotection, followed by purification, are carried out as described in Example 1.

The two stereoisomers are separated, and MS analysis shows values of 1655.85 and 1655.81 Da, respectively, which agree with the calculated value of 1655.79. The optical rotations are also measured on a photoelectric polarimeter as $[\alpha]_D^{20}$=$-36.0°$ and +6.0°±1.0(c=1, 50% acetic acid). Assaying the betides using the standard in vivo rat ovulation test shows that the first isomer is fully active (0/8) at 2.5μ gram, and at a dosage of 1μ gram, 5 out of 8 rats ovulated. The second isomer, at a dosage of 2.5μ gram, is only partially active with 7 out of 8 rats ovulating.

EXAMPLE 3C

The synthesis set forth in Example 3 is repeated; however, this time Fmoc(Me)-D/L-Agl(Boc) is coupled at the N-terminus. Upon deprotection, the methylamino side chain is reacted with 2-naphthoyl chloride as in Example 3. The betide having the formula Ac-D/L-Agl(methyl,2- naphthoyl)-D-4Cpa-D-3Pal-Ser-Aph(acetyl)-D-Aph(acetyl)-Leu-Lys (isopropyl)-Pro-D-Ala-NH$_2$ is produced. Following cleavage from the resin, deprotection and purification, as described with respect to Example 1, Betide No. 3C is obtained. The 2 stereoisomers are separated in the RP-HPLC purification, and the purity of each is estimated to be greater than 90%. MS analysis shows a mass of 1576.04 Da and 1576.02 Da, respectively, for the isomers which agree with the calculated mass of 1575.76 Da. Assaying the betides using the standard in vivo rat ovulation test shows that the first isomer is fully active at 2.5μ gram, and at a dosage of 1μ gram, only 2 out of 8 rats ovulate. The second isomer is only partially active at 5μ grams where 6 out of 8 rats ovulate.

EXAMPLE 4

The betide having the formula: Ac-D-2Nal-D-4Cpa-D-3Pal-Ser-(4-acetyl-amino-benzyl)D/L-amidoGly-D-Aph (acetyl)-Leu-Lys(isopropyl)-Pro-D-Ala-NH$_2$ is synthesized using the synthesis as set forth in Example 1. Instead of coupling NαBoc-D/L-Agl(Fmoc) in the 3-position, it is coupled in the 5-position, following acetylation of the D-Aph side chain. Ser is coupled in the 4-position, and the remainder of the chain completed as previously described. In this synthesis, following the completion of the decapeptide and the acetylation of the N-terminus, the following peptide intermediate is obtained: Ac-D-2Nal-(4Cl)D-Phe-D-3Pal-Ser(Bzl)-D/L-Agl(Fmoc)-D-Aph(Ac)-Leu-Lys(Ipr,Z)-Pro-D-Ala-NH-[MBHA resin support]. The side chain on the Agl residue is deprotected as in Example 1, and the intermediate is treated with 2 millimoles of acetyl-para-aminobenzoic acid (Ac-Paba) in DMF in the presence of HBTU for about 30 to 60 minutes at room temperature to acylate the side chain of the Agl residue.

The betidoresin is then subjected to the standard wash, and cleavage from the resin and deprotection, followed by purification, are carried out as described in Example 1. The resulting betide Ac-D-2Nal-(4Cl)D-Phe-D-3Pal-Ser-(4-acetyl-aminobenzyl)D/L-amidoGly-D-Aph(acetyl)-Leu-Lys(isopropyl)-Pro-D-Ala-NH$_2$ (Betide No. 4) is judged to be a 50/50 mixture of 2 isomers, and the purity is estimated to be greater than 80 percent. The optical rotation of the mixture is measured on a photoelectric polarimeter as $[\alpha]_D^{20}$=−18.9°±1 (c=1, 50% acetic acid) for the mixture of the two isomers. MS analysis shows the expected mass of 1561.8 Da. Assaying the betide mixture using the standard in vivo rat ovulation test shows that, at a dosage of 5 micrograms, only 2 out of 8 rats ovulate.

EXAMPLE 4A

The betide having the formula: Ac-D-2Nal-D-4Cpa-D-3Pal-Ser-(4 -acetyl-aminobenzyl, methyl)D/L-amidoGly-D-Apha(acetyl)-Leu-Lys(isopropyl)-Pro-D-Ala-NH$_2$ is synthesized by generally repeating the synthesis as set forth in Example 4 but coupling Fmoc(Me)-D/L-Agl in the 5-position. After the side chain on the Agl residue is deprotected, the newly freed methylamino groups are treated with 2 millimoles of acetyl-para-aminobenzoic acid (Ac-Paba) in DMF in the presence of HBTU for about 30 to 60 minutes at room temperature to acylate the side chain.

The betidoresin is then subjected to the standard wash, and cleavage from the resin and deprotection, followed by purification, are carried out as described in Example 1. The resulting betide Ac-β-D-2Nal-(4Cl)D-Phe-D-3Pal-Ser-(4-acetyl-aminobenzyl,methyl)D/L-amidoGly-D-Aph(acetyl)-Leu-Lys(isopropyl)-Pro-D-D-Ala-NH$_2$ (Betide No. 4A) is judged to be a 50/50 mixture of 2 isomers, and the purity is estimated to be greater than 90%. MS analysis shows a mass of 1575.86 Da which agrees with the calculated mass of 1575.76 Da.

Assaying the betide mixture using the standard in vivo rat ovulation test shows that it is fully active (0/8) at a dosage of 2.5 μg and at a dosage of 1 microgram, 5 out of 8 rats ovulate.

EXAMPLE 5

The betide having the formula: Ac-D-2Nal-D-4Cpa-D-3Pal-Ser-Aph(acetyl)-γ-(4-acetamidophenyl)D/L-amidoGly-Leu-Lys(isopropyl)-Pro-D-Ala-NH$_2$ is synthesized using the synthesis as set forth in Example 1. Instead of coupling N$^\alpha$Boc-D/L-Agl(Fmoc) in the 3-position, it is coupled in the 6-position, and D-3Pal is coupled in the 3 position. Immediately following the coupling of Agl, the Fmoc group is removed, and a reaction is carried out with Paba(Fmoc) as very generally described in Example 4. Following a wash with DCM, Boc is removed from the N-terminus of the chain, and N$^\beta$Boc-Aph(Fmoc) is next coupled to create the following betide intermediate: Boc-Aph(Fmoc)-D/L-Agl(aminobenzyl)(Fmoc)-Leu-Lys(Ipr,Z)-Pro-D-Ala-NH-[MBHA resin support]. The side chains on both the Agl and Aph residues are then simultaneously deprotected by removal of the Fmoc protection using 20 percent piperidine in DMF (10 ml) for about 30 minutes. After washing with DMF, the piperidine/DMF treatment is repeated. After a final wash with DMF, the intermediate is treated with a large excess of acetic anhydride in DCM for about 10 minutes at room temperature to simultaneously acetylate the side chains of both these residues. The completion of the synthesis is then carried out by adding the remaining 4 amino acids and acetylating the N-terminus as in Example 4.

The betide resin is then subjected to the standard wash, and cleavage from the resin, deprotection, and purification are carried out as described in Example 1. The resulting betide Ac-β-D-2Nal-(4Cl)D-Phe-D-3Pal-Ser-Aph(acetyl)-γ-(4-acetamidophenyl)D/L-amidoGly-Leu-Lys(isopropyl)-Pro-D-Ala-NH$_2$ (Betide No. 5) is judged to be a 50/50 mixture of two isomers, and the purity is estimated to be greater than 80 percent. The optical rotation is measured on a photoelectric polarimeter as $[\alpha]_D^{22}$=−27.5°±1 (c=1, 50% acetic acid) as a mixture of isomers. MS analysis shows the expected mass of 1561.8 Da for both isomers.

Assaying the mixture using the standard in vivo rat ovulation test shows that, at a dosage of 5.0 micrograms, 1 out of 8 rats ovulate and at a dosage of 2.5 micrograms, 2 out of 8 rats ovulate.

EXAMPLE 5A

The synthesis as set forth in Example 5 is repeated with one change, Boc(Me)-D/L-Agl(Fmoc) is coupled in the 6-position in order to create the betide Ac-D-2Nal-D-4Cpa-D-3Pal-Ser-Aph(acetyl)-γ-(methyl,4-acetamidophenyl)D/L-amidoGly-Leu-Lys(isopropyl)-Pro-D-Ala-NH$_2$. Instead of removing the Fmoc protection from the Agl residue immediately following its coupling, the Boc protecting group is first removed, and the free methylamino group is acylated with Ac-Paba in DMF as in Example 4. Following washing, the Fmoc protection is removed, and the synthesis as described with respect to Example 5 is repeated in order to complete the peptide intermediate.

The betide resin is then subjected to the standard wash, and cleavage from the resin, deprotection, and purification are carried out as described in Example 1. The resulting betide Ac-β-D-2Nal-(4Cl)D-Phe-D-3Pal-Ser-Aph(acetyl)-γ-(methyl,4-acetamidophenyl)D/L-amidoGly-Leu-Lys (isopropyl)-Pro-D-Ala-NH$_2$ (Betide No. 5A) is judged to be a 50/50 mixture of 2 isomers. The two isomers are separated by RP-HPLC and the purity of each is estimated to be greater than 80 percent. MS analysis shows the masses of 1575.82 Da and 1575.80 Da for the two isomers, respectively, which agree with the calculated value of 1575.76 Da. Assaying using the standard in vivo rat ovulation test shows that, at a dosage of 2.5 micrograms for the first isomer, 6 out of 8 rats ovulate, and at a dosage of 2.5 micrograms for the other, only 2 out of 8 rats ovulate.

EXAMPLE 6

The betide having the formula Ac-D-2Nal-D-4Cpa-D-3Pal-Ser-Aph(acetyl)-D-Aph(acetyl)-Agl(methyl,acetyl)-Lys(isopropyl)-Pro-D-Ala-NH$_2$ (Betide No. 6) is synthesized using the synthesis as set forth in Example 1. Instead of coupling N$^\alpha$Boc-D/L-Agl(Fmoc) in the 3-position, Fmoc (Me)-D/L-Agl(Boc) is coupled in the 7-position, as a precursor to Agl(methyl,acetyl), and D-3Pal is coupled in the 3-position. In this synthesis, following the coupling of the first 4 residues, deprotection of the primary amino group of Agl is carried out, followed by the coupling of the additional 6 residues. The following peptide intermediate is obtained: Boc-D-2Nal-D-Cpa-D-3Pal-Ser(Bzl)-Aph(Fmoc)-D-Aph (Fmoc)-D/L-Agl(methyl,Fmoc)-Lys(Ipr,Z)-Pro-D-Ala-NH-[MBHA resin support]. The side chains on the Aph residue, the D-Aph residue and the Agl(Me) residue are then deprotected by removal of the Fmoc using piperidine as in Example 1. The Boc group at the N-terminus is removed by treatment with 60% TFA in DCM for about 20 minutes. After a final wash with DMF, the intermediate is treated with a large excess of acetic anhydride in DCM for about 10 minutes at room temperature to simultaneously acetylate the side chains of these 3 residues and the N-terminus.

The betidoresin is then subjected to the standard wash, and cleavage from the resin and deprotection, followed by purification, are carried out as described in Example 1. The betide Ac-D-2Nal-D-4Cpa-D-3Pal-Ser-Aph(acetyl)-D-Aph (acetyl)-D/L-Agl(methyl,acetyl)-Lys(isopropyl)-Pro-D-Ala-NH$_2$ (Betide No. 6) is judged to be a 50/50 mixture of two isomers respectively having D- and L-Agl(Me,Ac) at position 7, and the purity is estimated to be greater than 80 percent. MS analysis shows a mass of 1547.76 Da for the mixture, which agrees with the calculated mass of 1547.72 Da.

Assaying the betide mixture using the standard in vivo rat anti-ovulation test shows that, at a dosage of 10 micrograms, 0 out of 8 rats ovulate and at a dosage of 2.5 micrograms, 2 out of 8 rats ovulate.

EXAMPLE 6A

The synthesis set forth in Example 6 is repeated using Boc-D/L-Agl(Fmoc) to provide the 7-position residue en route to creating the betide having the formula Ac-D-2Nal-D-4Cpa-D-3Pal-Ser-Aph(acetyl)-D-Aph(acetyl)-Agl (isobutyryl)-Lys(isopropyl)-Pro-D-Ala-NH$_2$ (Betide No. 6A). In this instance, the chain elongation synthesis is halted following the coupling of the D/L-Agl residue, and the Fmoc group is removed to deprotect the amino group that will ultimately constitute the side chain of the 7-position residue. Following removal, reaction is carried out with isobutyric anhydride in DCM for about 10 minutes at room temperature to acylate the free amino group. Following the standard wash, the Boc protecting group is removed, and the synthesis is completed as described in Example 6.

The betidoresin is then subjected to the standard wash, and cleavage from the resin and deprotection, followed by purification, are carried out as described in Example 1. The betide Ac-D-2Nal-D-4Cpa-D-3Pal-Ser-Aph(acetyl)-D-Aph (acetyl)-D/L-Agl(isobutyryl)-Lys(isopropyl)-Pro-D-Ala-NH$_2$ (Betide No. 6A) is judged to be a 50/50 mixture of two isomers respectively having D- and L-Agl(isobutyryl) at position 7, and the purity is estimated to be greater than 90%. MS analysis shows a mass of 1561.78 Da for the mixture, which agrees with the calculated mass of 1561.74 Da.

Assaying the betide mixture using the standard in vivo rat anti-ovulation test shows that, at a dosage of 10 micrograms, 0 out of 8 rats ovulate; at a dosage of 2.5 micrograms, 0 out of 8 rats ovulate; and at 1 microgram, 6 out of 8 rats ovulate.

EXAMPLE 6B

The synthesis set forth in Example 6 is again repeated, using Boc(Me)-D/L-Agl(Fmoc) and following the general pattern described in Example 6A to produce a betide having the formula Ac-D-2Nal-D-4Cpa-D-3Pal-Ser-Aph(acetyl)-D-Aph(acetyl)-Agl(methyl,isobutyryl)-Lys(isopropyl)-Pro-D-Ala-NH$_2$ (Betide No. 6B). In this instance, following the coupling of the D/L-Agl residue, the Boc protecting group is removed, and a reaction is carried out as previously described with isobutyric anhydride to acylate the secondary amino group. Following the standard wash, the Fmoc protecting group is removed from the Agl residue, and the chain elongation synthesis and modification of the Aph residues are carried out as described in Example 6.

The betidoresin is then subjected to the standard wash, and cleavage from the resin and deprotection, followed by purification, are carried out as described in Example 1. The betide Ac-D-2Nal-D-Cpa-D-3Pal-Ser-Aph(acetyl)-D-Aph (acetyl)-D/L-Agl(methyl,isobutyryl)-Lys(isopropyl)-Pro-D-Ala-NH$_2$ (Betide No. 6B) is judged to be a 50/50 mixture of two isomers respectively having D- and L-Agl(Me, isobutyryl) at position 7, and the purity is estimated to be greater than 80%. MS analysis shows a mass of 1575.80 Da for the mixture which agrees with the calculated mass of 1575.75 Da.

Assaying the betide mixture using the standard in vivo rat anti-ovulation test shows that, at a dosage of 2.5 micrograms, 0 out of 8 rats ovulate and at a dosage of 1 microgram, only 2 out of 8 rats ovulate.

EXAMPLE 6C

The synthesis set forth in Example 6 is repeated with some modifications in order to provide the betide having the formula Ac-D-2Nal-D-4Cpa-D-3Pal-Ser-Aph(acetyl)-D-Aph(acetyl)-Agl(acetyl)-Lys(isopropyl)-Pro-D-Ala-NH$_2$ (Betide No. 6C). In this instance, the chain elongation synthesis is continued through the coupling of the D/L-Agl residue and the 2 Aph residues. Then the Fmoc groups are removed to deprotect all three amino groups. Following removal, reaction is carried out with acetic anhydride in DCM for about 10 minutes at room temperature to acetylate all 3 amino groups. Following the standard wash, the Boc protecting group is removed, and the synthesis is completed as described in Example 6.

The betidoresin is then subjected to the standard wash, and cleavage from the resin and deprotection, followed by purification, are carried out as described in Example 1. The betide Ac-D-2Nal-D-Cpa-D-3Pal-Ser-Aph(acetyl)-D-Aph (acetyl)-D/L-Agl(acetyl)-Lys(isopropyl)-Pro-D-Ala-NH$_2$ (Betide No. 6C) is judged to be a 50/50 mixture of two isomers respectively having D- and L-Agl(acetyl) at position 7, and the purity is estimated to be greater than 90%. The optical rotation of the mixture is measured on a photoelectric polarimeter as $[\alpha]_D^{20} = -18.1° \pm 1.0$ (c=1, 50% acetic acid). MS analysis shows a mass of 1534.7 Da for the mixture, which agrees with the calculated mass of 1534.68 Da.

Assaying the betide mixture using the standard in vivo rat anti-ovulation test shows that, at a dosage of 10 micrograms, 0 out of 8 rats ovulate, and at a dosage of 0.5 micrograms, 4 out of 8 rats ovulate.

EXAMPLE 7

The betide having the formula Ac-D-2Nal-D-4Cpa-D-3Pal-Ser-Aph(acetyl)-D-Aph(acetyl)-Leu-D/L-Agl(Ac-β-Ala)-Pro-D-Ala-NH$_2$ (Betide No. 7) is synthesized using the synthesis as set forth in Example 1. Instead of coupling N$^\alpha$Boc-D/L-Agl(Fmoc) in the 3-position, it is coupled in the 8-position, and D-3Pal is coupled in the 3-position. In this synthesis, following the coupling of the first 3 residues, the side chain on the Agl residue is deprotected by removal of the Fmoc protection as in Example 1, and the intermediate is treated with β-Ala(acetyl) using a suitable coupling agent, such as DIC or DCC. Then, the protected D-Aph residues are coupled, and following simultaneous deprotection by Fmoc removal, the intermediate is treated with acetic anhydride in DCM for about 10 minutes at room temperature to simultaneously acetylate the side chains of 2 Aph residues. The betidoresin is then subjected to the standard wash, and the synthesis is completed using the method as generally taught in Example 1.

Cleavage from the resin and deprotection of the 4- and 8-position residues, followed by purification, are carried out as described in Example 1. The betide Ac-D-2Nal-(4Cl)D-Phe-D-3Pal-Ser-Aph(acetyl)-D-Aph(acetyl)-Leu-D/L-Agl (acetyl-β-Ala)-Pro-D-Ala-NH$_2$ (Betide No. 7) is judged to be a 50/50 mixture of two isomers respectively having D- and L-isomers at position 8, and the purity is estimated to be greater than 80 percent. The optical rotation of the mixture is measured on a photoelectric polarimeter as $[\alpha]_D^{20}$=-12.0°±1 (c=1, 50% acetic acid). MS analysis shows a mass for the mixture of 1505.7 which agrees with the expected mass of 1505.68 Da. RP-HPLC shows that the mixture is more hydrophilic than Acyline.

Assaying the betide mixture using the standard in vivo rat anti-ovulation test shows that, at a dosage of 5 micrograms, 0 out of 11 rats ovulate and at a dosage of 2.5 micrograms, 3 out of 9 rats ovulate.

EXAMPLE 7A

The synthesis as described in Example 7 is repeated with one change. Boc(Me)-D/L-Agl(Fmoc) is coupled in the chain to constitute the 8-position residue. The Boc protection is removed, and a reaction is carried out with Z-isopropyl-β-Ala using DIC or DCC as a coupling agent. After the standard wash, the Fmoc protecting group is removed, and the chain elongation synthesis is continued to couple the 7-, 6- and 5-position residues. Following acetylation of the side chains of the amino-Phe residues in the 5- and 6-positions, the chain elongation synthesis is completed using the method as generally taught in Example 1.

Cleavage from the resin effects removal of Z from the secondary amino group and deprotection of the other protected residues, and it is followed by purification as described in Example 1. The betide having the formula Ac-D-2Nal-(4Cl)D-Phe-D-3Pal-Ser-Aph(acetyl)-D-Aph(acetyl)-Leu-D/L-Agl(methyl,isopropylβ-alanyl)-Pro-D-Ala-NH$_2$ (Betide No. 7A) is judged to be a 50/50 mixture of two isomers, and the purity is estimated to be greater than 90%. The two separate stereoisomers are separated by the RP-HPLC treatment, and MS analysis show masses of 1561.79 Da and 1561.81 Da, respectively, for the two isomers, which agrees with the calculated mass of 1561.74 Da.

Assaying the betides using the standard in vivo rat ovulation test shows that the first isomer is fully active (0/8) at 2.5 μg and is also fully active at 1 μg (0/8); at 0.5 μg, only 5 out of 8 rats ovulate. The second isomer shows only partial activity at 2.5 micrograms, with 7 out of 8 rats ovulating.

EXAMPLE 7B

The synthesis as described in Example 7 is repeated with one change to create the betide: Ac-D-2Nal-D-4Cpa-D-3Pal-Ser-Aph(acetyl)-D-Aph(acetyl)-Leu-D/L-Agl(guanidinoacetyl)-Pro-D-Ala-NH$_2$. After coupling Boc-D/L-Agl(Fmoc), which is to constitute the 8-position residue, the Fmoc protection is removed, and a reaction is carried out with Fmoc-Gly using DCC as a coupling Agent. After the standard wash, the Boc protecting group is removed, and the chain elongation synthesis is continued to complete the synthesis of the decapeptide, coupling Boc-D-Aph(Ac) and Boc-Aph(Ac) as the 6- and 5-position residues. Following deprotection of the N-terminus, acetylation of the N-terminus is carried out using the acetic anhydride as generally taught in Example 1. At the end of the synthesis, the Fmoc protection is removed from Gly in the 8-position side chain and the amino function is reacted with 3,5-dimethyl-pyrazole-1-carboxamidine nitrate to generate the guanidino moiety.

Cleavage from the resin and deprotection followed by purification are carried out as described in Example 1. The betide (Betide No. 7B) is judged to be a 50/50 mixture of 2 isomers, and the purity is estimated to be greater than 90%. MS analysis show a mass of 1534.03 Da for the mixture of two isomers, which agrees with the calculated mass of 1533.68 Da. The optical rotation of the mixture is measured on a photoelectric polarimeter as $[\alpha]_D^{20}$=-16.2°±1.0(c=1, 50% acetic acid).

Assaying the betide mixture using the standard in vivo rat ovulation test shows that it is fully active (0/4) at 5 μg and at 2.5 μg, only 1 out of 7 rats ovulate. At 1.0 microgram, 3 out of 4 rats ovulate.

EXAMPLE 8

The betide having the formula Ac-D-2Nal-D-4Cpa-D-3Pal-Ser-Aph(acetyl)-D-Aph(acetyl)-Leu-Lys(isopropyl)-Pro-D/L-Agl(For)-NH$_2$ is synthesized using the synthesis as set forth in Example 1. Instead of coupling N$^\alpha$Boc-D/L-Agl (Fmoc) in the 3-position, it is coupled in the 10-position, and D-3Pal is coupled in the 3-position. In this synthesis, following the completion of the decapeptide and the acetylation of the N-terminus, the following peptide intermediate is obtained:Ac-D-2Nal-4Cl-D-Phe-D-3Pal-Ser(Bzl)-Aph(Ac)-D-Aph(Ac)-Leu-Lys(Ipr,Z)-Pro-D/L-Agl(Fmoc)-NH-[MBHA resin support]. The side chain on the Agl residue is then deprotected as in Example 1, and the intermediate is treated with excess formic acid in the presence of acetic anhydride, for about 40 minutes at room temperature to acylate the side chain of the Agl residue.

The betidoresin is then subjected to the standard wash, and cleavage from the resin and deprotection, followed by purification using two different buffer systems, are carried out as described in Example 1. The betide Ac-D-2Nal-4Cl-D-Phe-D-3Pal-Ser-Aph(acetyl)-D-Aph(acetyl)-Leu-Lys (isopropyl)-Pro-D/L-Agl(For)-NH$_2$ (Betide No. 8) is judged to be a mixture of 2 isomers, and the purity is estimated to be greater than 90%. The two stereoisomers are separated by RP-HPLC purification, and the optical rotations are measured on a photoelectric polarimeter as $[\alpha]_D^{20}$=-43° and -57°±1 (c=1, 50% acetic acid) respectively, for the two isomers. MS analysis shows the expected mass of 1561.74 Da and 1561.76, respectively, for the two isomers.

Assaying the betides using the standard in vivo rat ovulation test shows that the first isomer is active at 1 μg, with only 6 out of 17 rats ovulating, and the first isomer is partially active at 0.5 μg with 9 out of 11 rats ovulating. The second isomer is fully active (0/8) at 2.5 μg, but is inactive at a dosage of 1 μg. The first isomer exhibits very long duration of bioactivity, i.e. remaining fully active after 72 hours after testing as in Example 1.

EXAMPLE 8A

The synthesis set forth in Example 8 is repeated, substituting Boc-D/L-Agl(Z) and omitting acylation of the side chain amino group of Agl. Cleavage from the resin and deprotection, followed by purification, are carried out as described in Example 1. The betide Ac-D-2Nal-(4Cl)D-Phe-D-3Pal-Ser-Aph(acetyl)-D-Aph(acetyl)-Leu-Lys(isopropyl)-Pro-D/L-Agl-NH$_2$ (Betide No. 8A) is judged to be a 50/50 mixture of 2 isomers, and the purity is estimated to be greater than 90%. The optical rotation of the mixture is measured on a photoelectric polarimeter as $[\alpha]_D^{20}$=−37.3°±1 (c=1, 50% acetic acid). MS analysis showed the mass of 1533.86 Da for the mixture which agrees with the calculated mass of 1533.74 Da. The betides are more hydrophilic than Acyline.

Assaying the betide mixture in the standard in vivo rat anti-ovulation test shows that, at a dosage of 2.5 micrograms, the mixture was fully active, with 0 out of 8 rats ovulating.

EXAMPLE 8B

The synthesis set forth in Example 8A is generally repeated; however this time, Fmoc-D/L-Agl(Me,Z) is coupled to the resin. Cleavage and purification are effected as described hereinbefore in Example 1 to produce the compound Ac-D-2Nal-(4Cl)D-Phe-D-3Pal-Ser-Aph(acetyl)-D-Aph(acetyl)-Leu-Lys(isopropyl)-Pro-D/L-Agl(methyl)-NH$_2$ (Compound No. 8A). MS analysis of the mixture shows a mass of 1547.8 Da which agrees with the calculated mass of 1547.76 Da.

The optical rotation of the mixture is measured on a photoelectric polarimeter as $[\alpha]_D^{20}$=−36.7°±1.0(c=1, 50% acetic acid).

Assaying the mixture in the standard in vivo rat anti-ovulation test shows that the mixture is fully active (0/8) at a dosage of 2.5 micrograms.

EXAMPLE 8C

The synthesis as described in Example 8 is again generally repeated; however, the Boc(Me)-D/L-Agl(Fmoc) is coupled to the resin. The Boc protecting group is removed, and acylation is carried out using formic acid/acetic anhydride as described in Example 8. The remainder of the synthesis is carried out as described in Example 8 after removal of the Fmoc group, and the betidoresin is then subjected to the standard wash. Cleavage from the resin and deprotection followed by purification using two different buffer systems are carried out as described in Example 1. The betide Ac-2Nal-4Cl-D-Phe-D-3Pal-Ser-Aph(acetyl)-D-Aph(acetyl)-Leu-Lys(isopropyl)-Pro-D/L-Agl(methyl,For)-NH$_2$ (Betide No. 8C) is judged to be a 50/50 mixture of 2 isomers, and the purity is estimated to be greater than 90%. MS analysis shows the mass of 1575.87 Da for the mixture, which agrees with the calculated mass of 1575.76 Da. The betide mixture is more hydrophilic than Acyline.

Assaying the betide mixture in the standard in vivo rat anti-ovulation test shows that it is fully active (0/8) at 2.5 microgram dosage, and it is nearly fully active at a dosage of 1 microgram, with only 1 out of 8 rats ovulating.

The foregoing compounds which were tested exhibit biological potency, from the standpoint of anti-ovulatory effect, such as is at least generally comparable to the corresponding GnRH antagonist peptide known as Acyline of which each is an analog. As a result of extensive testing in this area for over a decade, biopotency determined in this widely accepted test constitutes evidence as to biopotency of such compounds to suppress gonadotropin secretion. Based upon superior solubility, resistance to in vivo gelling and other properties, these compounds are considered to be particularly useful as anti-ovulatory agents and more generally to suppress the secretion of gonadotropins and inhibit the release of steroids by the gonads.

The compounds of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. For example, an aqueous solution of the peptide can be repeatedly treated with 1N acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 10 micrograms to about 2.5 milligrams of the peptide per kilogram of the body weight of the host when given intravenously. Oral dosages might be higher; however, the nature of these compounds should permit effective oral administration. Overall, treatment of subjects with these peptides is generally carried out in the same manner as the clinical treatment using other antagonists of GnRH using a suitable carrier in which the compound is soluble.

It may also be desirable to deliver the GnRH analog over prolonged periods of time, for example, for periods of one week to one year from a single administration, and slow release, depot or implant dosage forms may be utilized. For example, a suitable, slow-release depot formulation for injection may contain the GnRH antagonist or a salt thereof dispersed or encapsulated in a slow degrading, non-toxic or non-antigenic polymer such as a polylactic acid/polyglycolic acid polymer, for example, as described in U.S. Pat. No. 3,773,919. It is known to administer such slow-release dosage formulations by a poultice that may be applied within the mouth. These compounds may also be formulated into silastic implants.

These compounds can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation- or chemotherapy. They are also useful for treatment of steroid-dependent tumors. Effective dosages will vary with the form of administration and the particular species of mammal being treated. An example of one typical dosage form is a bacteriostatic water solution at a pH of about 6 containing the peptide which solution is administered parenterally to provide a dose in the range of about 0.1 to 2.5 mg/kg of body weight per day. These compounds are considered to be well-tolerated in vivo and to resist gelling; accordingly, they are considered to be particularly wellsuited for administration by subcutaneous injection in a bacteriostatic water solution at appropriate concentrations, above about 0.75 mg/ml and even above about 1.0 mg/ml, without danger of gelling at the point of injection.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. An acylating agent can be attached to the amino Phe residue and thereafter coupled to the peptide chain rather than modifying it while a part of the chain. D-2Pal and D-4Pal are considered to be equivalents of D-3Pal. Other equivalent acylating groups can be used instead of acetyl at the N-terminus. Other substituted D-Phe, such as (4F)D-Phe, can be used in the 2-position. Instead of Aph(Ac), the aminophe group can be treated with alternative acylating agents as disclosed in International Application WO 95/25741, such as formyl,β-Ala(atz) and gamma-aminobutyric acid(atz), which likewise result in GnRH antagonists that exhibit long-acting duration; thus, these are considered equivalents of D- and L-Aph(Ac), respectively. Both butyl Lys and diethyl Lys are considered to be equivalents of ILys; however, ILys is most preferred. Other hydrophobic amino acid residues can also be employed in the 1-position, preferably in D-isomer form, and are considered equivalents of those specified. The betidamino acids which may be present in the 1-, 3-, 6- and 10-positions may be either in the D-isomer form or in the D/L-isomer form, which are considered equivalents. The betidamino acids in the 4-, 5-, 7- and 8-positions may be in the L-isomer form or in the D/L-isomer form, which are considered equivalents. Moreover, the antagonists can be administered in the form of their pharmaceutically or veterinarially acceptable, nontoxic salts, as indicated hereinbefore, which are considered equivalents. Particular features of the invention are emphasized in the claims which follow.

What is claimed is:

1. A GnRH antagonist having the following formula:

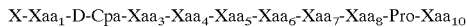

wherein X is an acyl group of 7 carbon atoms or less; $Xaa_1$ is D-2Nal or a corresponding betidamino acid; $Xaa_3$ is D-3Pal or a corresponding betidamino acid; $Xaa_4$ is Ser or a corresponding betidamino acid; $Xaa_5$ is 4Aph(Q) or a corresponding betidamino acid; $Xaa_6$ is D-4Aph(Q) or a corresponding betidamino acid; $Xaa_7$ is Leu or a corresponding betidamino acid; $Xaa_8$ is ILys or a corresponding betidamino acid; $Xaa_{10}$ is D-Ala-$NH_2$ or a corresponding betidamino acid; and Q is 3-amino 1,2,4 triazole(atz) or acetyl (Ac); provided that at least one Xaa is a betidamino acid.

2. A GnRH antagonist according to claim 1 wherein Q is acetyl.

3. A GnRH antagonist according to claim 1 wherein Q is atz.

4. A GnRH antagonist according to claim 1 wherein $Xaa_1$ is Agl(2-naphthoyl) or Agl(methyl, 2-naphthoyl).

5. A GnRH antagonist according to claim 1 wherein $Xaa_3$ is Agl(3-pyridyl), Agl(4-pyridyl), Agl(methyl, 3-pyridyl), or Agl(methyl, 4-pyridyl).

6. A GnRH antagonist according to claim 1 wherein $Xaa_4$ is Agl(formyl) or Agl(methyl,formyl).

7. A GnRH antagonist according to claim 1 wherein $Xaa_5$ is Agl(4-acetyl-aminobenzoyl).

8. A GnRH antagonist according to claim 1 wherein $Xaa_6$ is Agl(4-acetyl-aminobenzoyl).

9. A GnRH antagonist according to claim 1 wherein $Xaa_7$ is Agl(isobutyryl), Agl(methyl,isobutyryl) or Agl(methyl,acetyl).

10. A GnRH antagonist according to claim 1 wherein $Xaa_8$ is Agl(isopropylglycyl), Agl(methyl, isopropyl-β-Ala) or Agl(guanidinoacetyl).

11. A GnRH antagonist according to claim 1 wherein $Xaa_{10}$ is Agl(formyl) or Agl(methyl,formyl).

12. A GnRH antagonist having the following formula:
Ac-$Xaa_1$-D-Cpa-$Xaa_3$-$Xaa_4$-4Aph(Q)-D-4Aph(Q)-$Xaa_7$-$Xaa_8$-Pro-$Xaa_{10}$ wherein $Xaa_1$ is D-2Nal or a corresponding betidamino acid; $Xaa_3$ is D-3Pal or a corresponding betidamino acid; $Xaa_4$ is Ser or a corresponding betidamino acid; $Xaa_7$ is Leu or a corresponding betidamino acid; $Xaa_8$ is ILys or a corresponding betidamino acid; $Xaa_{10}$ is D-Ala-$NH_2$ or a corresponding betidamino acid; and Q is 3-amino 1,2,4 triazole or acetyl; provided that at least one Xaa is betidamino acid.

13. A GnRH antagonist according to claim 12 wherein Q is acetyl.

14. A GnRH antagonist according to claim 12 wherein Q is 3-amino 1,2,4 triazole.

15. A GnRH antagonist having the formula:
Ac-$Xaa_1$-D-Cpa-$Xaa_3$-$Xaa_4$-4Aph(Q)-D-4Aph(Q)-$Xaa_7$-$Xaa_8$-Pro-$Xaa_{10}$ wherein:

$Xaa_1$ is (a)

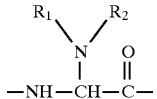

with $R_1$ being H or $CH_3$, and $R_2$ being 2-naphthoyl, or (b) D-2Nal;

wherein $Xaa_3$ is (a) D- or D/L-Agl(nicotinoyl) or D- or D/L-Agl(isonicotinoyl), or (b) D-3Pal;

wherein $Xaa_4$ is (a)

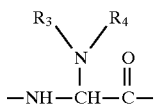

with $R_3$ being H or $CH_3$ and $R_4$ being formyl or hydroxyacetyl, or (b) Ser;

wherein

Q is Ac or atz;

wherein $Xaa_7$ is (a) L- or D/L-Agl(isobutyryl) or L- or D/L-Agl(methyl,isobutyryl), or (b) Leu;

wherein $Xaa_8$ is (a)

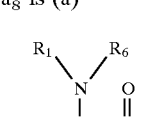

with $R_1$ being H or $CH_3$ and $R_6$ being (isopropyl)β-alanyl, (isopropyl)glycyl, or guanidinoacetyl; or (b) ILys, and wherein Xaa₁₀ is (a)

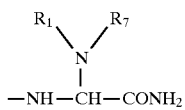

with R₁ being H or CH₃ and R₇ being H or formyl, or (b) D-Ala-NH₂, provided that at least one of Xaa₁, Xaa₃, Xaa₄, Xaa₈ and Xaa₁₀ is (a).

16. A GnRH antagonist according to claim 15 wherein Q is acetyl.

17. A GnRH antagonist according to claim 15 wherein Q is Atz.

18. A GnRH antagonist according to claim 15 wherein Xaa₄ is L- or D/L-Agl(For).

19. A GnRH antagonist according to claim 15 wherein Xaa₁₀ is D- or D/L-Agl(For).

20. A GnRH antagonist according to claim 15 wherein Xaa₈ is L- or D/L-Agl(methyl,isopropyl-β-Ala).

* * * * *